(12) United States Patent
Vortman et al.

(10) Patent No.: US 11,103,731 B2
(45) Date of Patent: Aug. 31, 2021

(54) OVERCOMING ACOUSTIC FIELD AND SKULL NON-UNIFORMITIES

(71) Applicants: Kobi Vortman, Haifa (IL); Shuki Vitek, Haifa (IL); Eyal Zadicario, Tel Aviv-Jaffa (IL); Yoav Levy, Hinanit (IL)

(72) Inventors: Kobi Vortman, Haifa (IL); Shuki Vitek, Haifa (IL); Eyal Zadicario, Tel Aviv-Jaffa (IL); Yoav Levy, Hinanit (IL)

(73) Assignee: INSIGHTEC, LTD., Tirat Carmel (IL)

( * ) Notice: Subject to any disclaimer, the term of this patent is extended or adjusted under 35 U.S.C. 154(b) by 785 days.

(21) Appl. No.: 15/404,412

(22) Filed: Jan. 12, 2017

(65) Prior Publication Data

US 2018/0193675 A1   Jul. 12, 2018

(51) Int. Cl.
| | |
|---|---|
| *A61N 7/02* | (2006.01) |
| *A61B 5/055* | (2006.01) |
| *A61B 8/08* | (2006.01) |
| *A61N 7/00* | (2006.01) |
| *A61B 18/00* | (2006.01) |
| *A61B 90/00* | (2016.01) |

(52) U.S. Cl.
CPC ............... *A61N 7/02* (2013.01); *A61B 5/055* (2013.01); *A61B 8/485* (2013.01); *A61B 2018/00714* (2013.01); *A61B 2018/00761* (2013.01); *A61B 2018/00791* (2013.01); *A61B 2090/374* (2016.02); *A61N 2007/0078* (2013.01); *A61N 2007/0095* (2013.01)

(58) Field of Classification Search
CPC ........... A61B 2018/00791; A61B 2018/00714; A61B 2018/00761; A61N 2007/0095; A61N 2007/0078
See application file for complete search history.

(56) References Cited

U.S. PATENT DOCUMENTS 6,419,648 B1 *  7/2002  Vitek ..................... A61N 7/02
                                                        601/3
7,652,410 B2 *  1/2010  Prus ...................... B06B 1/0622
                                                        310/334
(Continued)

FOREIGN PATENT DOCUMENTS

| EP | 0627206 | 12/1994 |
|---|---|---|
| WO | 0243805 A1 | 6/2006 |
| WO | WO-2015160708 A1 * | 10/2015 |

OTHER PUBLICATIONS

International Search Report, for International Application No. PCT/IB2017/001689, dated Aug. 5, 2018, 15 pages.

*Primary Examiner* — Lynsey C Eiseman
*Assistant Examiner* — Amanda L Steinberg
(74) *Attorney, Agent, or Firm* — Morgan, Lewis & Bockius LLP

(57) ABSTRACT

Various approaches for heating a target region substantially uniformly include identifying one or more locations of one or more hot spots in the target region and/or surrounding regions of the target region during an ultrasound sonication process; computing a temporal variation to an output parameter of at least one of the transducer elements based at least in part on the identified location(s) of the hot spot(s); and operating the at least one transducer element to achieve the temporal variation of the output parameter so as to minimize the hot spot(s).

15 Claims, 10 Drawing Sheets

(56) References Cited

U.S. PATENT DOCUMENTS

| | | | |
|---|---|---|---|
| 9,579,518 B2 * | 2/2017 | Gertner | A61B 5/4839 |
| 2011/0270136 A1 * | 11/2011 | Vitek | A61N 7/02 |
| | | | 601/2 |
| 2012/0029396 A1 * | 2/2012 | Vortman | A61N 7/02 |
| | | | 601/2 |
| 2013/0296743 A1 | 11/2013 | Lee et al. | |
| 2014/0276248 A1 * | 9/2014 | Hall | A61N 1/3603 |
| | | | 601/2 |
| 2015/0025360 A1 | 1/2015 | Levy et al. | |
| 2018/0191020 A1 * | 7/2018 | Melack | H01M 2/0285 |
| 2018/0193675 A1 * | 7/2018 | Vortman | A61B 8/485 |

* cited by examiner

OVERCOMING ACOUSTIC FIELD AND SKULL NON-UNIFORMITIES

FIELD OF THE INVENTION

The field of the invention relates generally to thermal energy treatment systems and, more particularly, to systems and methods for overcoming non-uniformities in an acoustic field transmitted through non-uniform tissue, such as the skull.

BACKGROUND

The treatment of cancer patients often involves applying thermal energy to tissues or tissue interfaces. For example, tumor control—i.e., the reduction of the size and/or growth rate of a tumor—may be accomplished by locally heating, and thereby coagulating or ablating, tumor tissue. Heat may also be used to alleviate pain in the vicinity of a tumor zone. Bone pain palliation, in particular, is often achieved by raising the temperature of the bone surface adjacent the tumor to a level that ablate the nerves in that region.

A commonly employed thermal treatment method is the focusing of ultrasound (i.e., acoustic waves having a frequency greater than about 20 kHz) into tissue to be treated (the "target"). Focused ultrasound methods may utilize, for example, a piezo-ceramic transducer that is placed externally to the patient but in close proximity to the target. The transducer converts an electronic drive signal into mechanical vibrations, resulting in the emission of acoustic waves (a process hereinafter referred to as "sonication"). The transducer may be shaped so that the waves converge in a focal zone. Alternatively or additionally, the transducer may be defined by a plurality of individually driven transducer elements whose phases (and, optionally, amplitudes) can each be controlled independently from one another and, thus, can be set so as to result in constructive interference of the individual acoustic waves in the focal zone. Such a "phased-array" transducer facilitates steering the focal zone to different locations by adjusting the relative phases between the transducers. Magnetic resonance imaging (MRI) may be utilized to visualize the focus and target in order to guide the ultrasound beam and potentially improve ultrasound focusing.

When applying thermal energy to tissues with ultrasound, it is important to heat the target region uniformly, i.e., to generate a homogeneous temperature distribution in the focal zone. Otherwise, local "hot spots" of an inhomogeneous temperature distribution can cause heating of unplanned targets and significant, at times intolerable, pain before the goal of the sonication (e.g., pain palliation in a surface area, or ablation of a tumor) is accomplished, and treatment may need to be stopped abruptly. Uniform heating is, however, often difficult to achieve. For example, physiological constraints on the placement of the transducer array with respect to the target may entail a need for beam steering, which, in turn, may result in an ultrasound propagation direction far from perpendicular to the tissue interfaces, a higher-order beam mode, or an elongated focus, all of which can adversely affect the uniformity of the beam.

In addition, inhomogeneity of intervening tissues located between the transducer array and the target region may distort the ultrasound beam and create one or more hot spots at locations other than the intended focal zone. As noted, such hot spots may lead to undesired heating, pain for the patient, and/or possibly necrosis of non-targeted tissue; even if within the target tissue, hot spots can be problematic by, for example, causing tissue necrosis outside the target region. Because each transducer is made up of a finite number of elements, the discrete phase changes used to change the phase between the elements may also contribute to the creation of secondary hot spots.

Accordingly, there is a need for systems and methods that reduce undesired hot spots in the target and non-target regions without substantially reducing the ultrasound intensity at the target region.

SUMMARY

Embodiments of the present invention minimize undesired local hot spots at the target region and/or non-target region by first identifying the locations thereof and adjusting parameters of the transducer array based on the identified locations to minimize the hot spots. (The term "hot spot" is herein used to connote a concentrated region of ultrasound energy that raises the temperature of the tissue in which it occurs to a clinically unacceptable level.) The locations of the undesired hot spots may be predicted using a physical model that simulates ultrasound field aberrations resulting from, for example, beams traversing inhomogeneous intervening tissue, transducer geometry and/or acoustic field design (e.g., for refocusing purposes). Alternatively, the hot spot locations may be measured using a temperature-sensitive device (e.g., a magnetic resonance imaging (MRI) device). In one embodiment, a tissue model characterizing the material characteristics of the target and/or surrounding tissue is used to identify one or more regions that are nearby the expected locations of the hot spots and have less heat sensitivity and/or tolerate higher thermal energy than tissues at the expected locations of the hot spots. The physical model can then inversely compute the required frequency associated with at least one transducer element to produce hot spots at the identified low-heat sensitive and/or high-thermal-energy tolerant region(s). In response to the physical model (and tissue model in some embodiments), a controller of the transducer element(s) may adjust the frequency of the transducer element(s) based on the computed frequency. In various embodiments, the controller of the transducer element(s) determines a dynamically varying pattern of the transducer frequencies such that the hot spot locations are shifted between their expected locations and the identified low-heat sensitive and/or high-thermal-energy tolerant region(s) to avoid any tissue damage. Alternatively, the controller of the transducer element(s) may randomly vary the frequency of the transducer element(s). As the frequencies of the transmitted waves change, the locations of the hot spots may vary; this disperses the ultrasound energy from the predicted hot spot locations to several other locations and thereby evens out the resulting temperature distribution while keeping a sufficiently high temperature at the target.

Alternatively or additionally, the physical model may adjust values of other transducer parameters to control the hot spots. For example, based on the expected locations of the hot spots, the physical model may simulate the effects, via varying the intensities (amplitudes) associated with at least some transducer elements, on an intensity ratio of the maximal intensity in a hot spot to the maximal intensity in the focal zone within the target. Based on the simulated effects, the wave intensities of some transducer elements may be adjusted to decrease the intensity ratio, thereby reducing the temperature at the undesired hot spots while maximizing the temperature at the target.

Compensation for the hot spots may also be achieved by selectively activating and deactivating at least some transducer elements. For example, the transducer array may be divided into multiple sub-regions; activation of different sub-regions may generate a common focal zone at the target region with undesired hot spots at various locations inside and/or outside the focal zone. In some embodiments, each sub-region of the transducer elements is selectively activated and deactivated so as to change the locations of the hot spots. This, again, results in energy dispersion from a relatively smaller number of hot spot locations to a larger number of hot spot locations and thereby improves the uniformity of the resulting temperature distribution.

In still other embodiments, beamforming is used to compensate for hot spots by controlling an interference pattern of the transmitted ultrasound waves. For example, adjusting a time delay (or alternatively described as a phase) associated with each transducer element may result in various interference patterns; each interference pattern may have wave amplifications, each corresponding to a hot spot, at different locations. Therefore, dynamically varying the time delays (or phases) associated with at least some of the transducer elements may also spatially distribute these hot spots, thereby temporarily reducing the hot spots so as to improve the uniformity of the temperature distribution.

Accordingly, in one aspect, the invention pertains to a method of heating a target region using an ultrasound transducer having multiple transducer elements. In various embodiments, the method includes identifying one or more locations of one or more hot spots having a time-averaged energy density above a predefined acceptable level in the target region and/or a region surrounding the target region during an ultrasound sonication process; based at least in part on the identified location(s) of the hot spot(s), computing a temporal variation to an output parameter (e.g., a frequency, an amplitude, a phase, and/or a time delay) of one or more transducer elements that will reduce the time-averaged energy density of the hot spot(s) to the predefined acceptable level; and operating the transducer element(s) to achieve the temporal variation of the output parameter. In one implementation, the temporal variation creates a substantially uniform temperature distribution in the target region.

The method may further include acquiring imaging data (e.g., ARFI data) of the target region and/or the surrounding region. A temperature distribution in the target region and/or the surrounding region may be determined based on the acquired imaging data. In addition, the location(s) of the hot spot(s) may be identified based on the temperature distribution. In various embodiments, an acoustic field distribution in the target region and/or the surrounding region is determined based on the acquired imaging data. In addition, the location(s) of the hot spot(s) may be identified based on the acoustic field distribution. In some embodiments, based on the acquired imaging data, a predicted temperature distribution in the target region and the surrounding region is generated using a prediction model; the location(s) of the hot spot(s) may be identified based on the predicted temperature distribution.

The location(s) of the hot spot(s) may be identified based at least in part on a prediction model. The temporal variation may be continuous or may include discrete steps during the ultrasound sonication process.

In another aspect, the invention relates to a method of heating a target region using an ultrasound transducer having multiple transducer elements. In various embodiments, the method includes dividing the ultrasound transducer into multiple sub-regions, each sub-region having multiple transducer elements; identifying one or more locations of one or more hot spots having an energy density above a predefined acceptable level in the target region and/or a region surrounding the target region during an ultrasound sonication process; based at least in part on the identified location(s) of the hot spot(s), computing an activation and deactivation pattern of each sub-region that will reduce the energy density of the hot spot(s) to the predefined acceptable level; and operating each sub-region of the transducer elements based at least in part on the activation and deactivation pattern. In one implementation, the activation and deactivation pattern creates a substantially uniform temperature distribution in the target region.

The method may further include acquiring imaging data (e.g., ARFI data) of the target region and/or the surrounding region. A temperature distribution in the target region and/or the surrounding region may be determined based on the acquired imaging data. In addition, the location(s) of the hot spot(s) may be identified based on the temperature distribution. In various embodiments, an acoustic field distribution in the target region and/or the surrounding region is determined based on the acquired imaging data. In addition, the location(s) of the hot spot(s) may be identified based on the acoustic field distribution. In some embodiments, based on the acquired imaging data, a predicted temperature distribution in the target region and the surrounding region is generated using a prediction model; the location(s) of the hot spot(s) may be identified based on the predicted temperature distribution. In addition, the location(s) of the hot spot(s) may be identified based at least in part on a prediction model.

Another aspect of the invention relates to a system for heating a target region. In various embodiments, the system includes an ultrasound transducer having multiple transducer elements and a controller configured to: (a) identify one or more locations of one or more hot spots having a time-averaged energy density above a predefined acceptable level in the target region and/or a region surrounding the target region during an ultrasound sonication process; (b) based at least in part on the identified location(s) of the hot spot(s), compute a temporal variation to an output parameter of one or more transducer elements that will reduce the time-averaged energy density of the hot spot(s) to the predefined acceptable level; and operate the transducer element(s) to achieve the temporal variation of the output parameter. In one implementation, the temporal variation creates a substantially uniform temperature distribution in the target region.

The system may further include an imager (e.g., an ARFI device), coupled to the controller, for acquiring imaging data of the target region and/or the surrounding region. The controller may be further configured to determine a temperature distribution in the target region and/or the surrounding region based on the imaging data, and identify the location(s) of the hot spot(s) based on the temperature distribution. In various embodiments, the controller is further configured to determining an acoustic field distribution in the target region and/or the surrounding region based on the imaging data, and identify the location(s) of the hot spot(s) based on the acoustic field distribution. In some embodiments, the controller is further configured to generate a predicted temperature distribution in the target region and the surrounding region based on the imaging data and a physical model, and identify the location(s) of the hot spot(s) based on the predicted temperature distribution.

In addition, the controller may be further configured to identify the location(s) of the hot spot(s) based at least in part on a prediction model. In some embodiments, the output parameter includes a frequency, an amplitude, a phase, and/or a time delay of a signal driving the transducer element(s). In one embodiment, the controller is further configured to continuously vary the output parameter based on the temporal variation. In another embodiment, the controller is further configured to vary the output parameter of the transducer element(s) in discrete steps based on the temporal variation.

In yet another aspect, the invention pertains to a system for heating a target region. In various embodiments, the system includes an ultrasound transducer having multiple transducer elements and a controller configured to: (a) divide the ultrasound transducer into multiple sub-regions, each sub-region having multiple transducer elements; (b) identify one or more location of one or more hot spots having an energy density above a predefined acceptable level in the target region and/or a region surrounding the target region during an ultrasound sonication process; (c) based at least in part on the identified location(s) of the hot spot(s), compute an activation and deactivation pattern of each sub-region that will reduce the energy density of the hot spot(s) to the predefined acceptable level; and (d) operate each sub-region of the transducer elements based at least in part on the activation and deactivation pattern. In one implementation, the activation and deactivation pattern creates a substantially uniform temperature distribution in the target region.

The system may further include an imager (e.g., an ARFI device), coupled to the controller, for acquiring imaging data of the target region and/or the surrounding region. The controller may be further configured to determine a temperature distribution in the target region and/or the surrounding region based on the imaging data, and identify the location(s) of the hot spot(s) based on the temperature distribution. In various embodiments, the controller is further configured to determining an acoustic field distribution in the target region and/or the surrounding region based on the imaging data, and identify the location(s) of the hot spot(s) based on the acoustic field distribution. In some embodiments, the controller is further configured to generate a predicted temperature distribution in the target region and the surrounding region based on the imaging data and a physical model, and identify the location(s) of the hot spot(s) based on the predicted temperature distribution. In addition, the controller may be further configured to identify the location(s) of the hot spot(s) based at least in part on a prediction model.

As used herein, the term "substantially" means±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1:
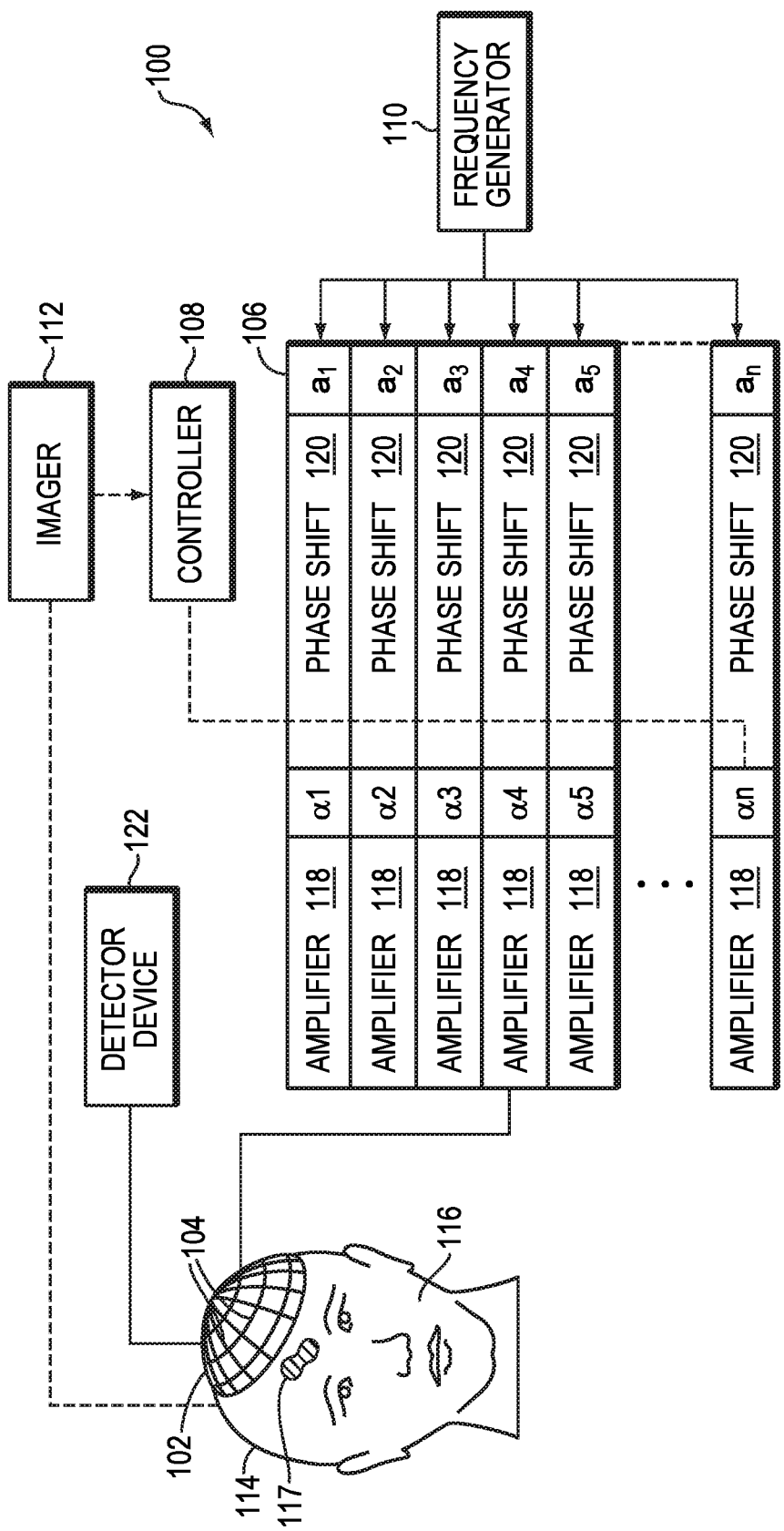
FIG. 1 illustrates a focused ultrasound system in accordance with various embodiments.

FIG. 1 illustrates an exemplary ultrasound therapy system 100 for focusing ultrasound onto a patient's brain through the skull. One of ordinary skill in the art, however, will understand that the ultrasound system 100 described herein may be applied to any part of the human body. In various embodiments, the system 100 includes a phased array 102 of transducer elements 104, a beamformer 106 driving the phased array 102, a controller 108 in communication with the beamformer 106, and a frequency generator 110 providing an input electronic signal to the beamformer 106. In various embodiments, the system further includes an imager 112, such as a magnetic resonance imaging (MRI) device, a computer tomography (CT) device, a positron emission tomography (PET) device, a single-photon emission computed tomography (SPECT) device, or an ultrasonography device, for determining anatomical characteristics of the skull 114 of a patient 116.

The array 102 may have a curved (e.g., spherical or parabolic) shape suitable for placing it on the surface of the skull 114 or a body part other than the skull, or may include one or more planar or otherwise shaped sections. Its dimensions may vary, depending on the application, between millimeters and tens of centimeters. The transducer elements 104 of the array 102 may be piezoelectric ceramic elements, and may be mounted in any materials suitable for damping the mechanical coupling between the elements 104. Piezocomposite materials, or generally any materials capable of converting electrical energy to acoustic energy, may also be used. To assure maximum power transfer to the transducer elements 104, the elements 104 may be configured to electrically match the input impedance.

The transducer array 102 is coupled to the beamformer 106, which drives the individual transducer elements 104 so that they collectively produce a focused ultrasonic beam or field at a target region 117. For n transducer elements, the beamformer 106 may contain n driver circuits, each circuit including or consisting of an amplifier 118 and a phase delay circuit 120; drive circuit drives one of the transducer elements 104. The beamformer 106 receives a radio frequency (RF) input signal, typically in the range from 0.1 MHz to 5.0 MHz, from the frequency generator 110. The input signal may be split into n channels for the n amplifiers 118 and delay circuits 120 of the beamformer 106. In some embodiments, the frequency generator 110 is integrated with the beamformer 106. The radio frequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $a_1$-$a_n$ imposed by the beamformer 106 serve to transmit and focus ultrasonic energy through the patient's skull 114 onto a selected region of the patient's brain, and account for wave distortions induced in the skull 114 and soft brain tissue. The amplification factors and phase shifts are computed using the controller 108, which may provide the computational functions through software, hardware, firmware, hardwiring, or any combination thereof. For example, the controller 108 may utilize a general-purpose or special-purpose digital data processor programmed with software in a conventional manner, and without undue experimentation, in order to determine the phase shifts and amplification factors necessary to obtain a desired focus or any other desired spatial field patterns. In certain embodiments, the computation is based on detailed information about the characteristics (e.g., structure, thickness, density, etc.) of the skull 114 and their known effects on propagation of acoustic energy. Such information may be obtained from the imager 112 as further described below. Image acquisition may be three-dimensional or, alternatively, the imager 112 may provide a set of two-dimensional images suitable for reconstructing a three-dimensional image of the skull 114 from which thicknesses and densities can be inferred. Conventional image-manipulation functionality may be implemented in the imager 112, in the controller 108, or in a separate device.

System 100 may be modified in various ways within the scope of the invention. For example, for diagnostic applications, the system may further include a detector device 122 that measures transmitted or reflected ultrasound, and which may provide the signals it receives to the controller 108 for further processing. The reflection and transmission signals may also be used as feedback for the phase and amplitude adjustments of the beamformer 106. The system 100 may contain a positioner for arranging the array 102 of transducer elements 104 with respect to the patient's skull 114. In order to apply ultrasound therapy to body parts other than the brain, the transducer array 102 may take a different (e.g., cylindrical, flat, etc.) shape. In some embodiments, the transducer elements 104 are mounted movably and rotatably, providing mechanical degrees of freedom that can be exploited to improve focusing properties. Such movable transducers may be adjusted by conventional actuators, which may be driven by a component of controller 108 or by a separate mechanical controller.

Figure 2:
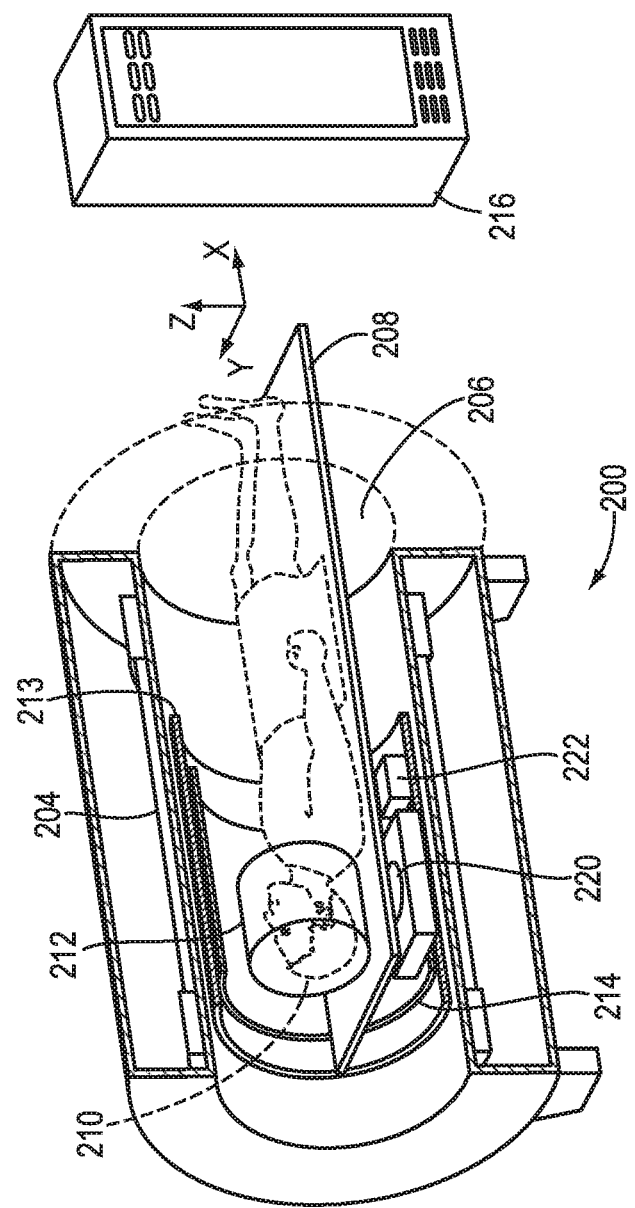
FIG. 2 schematically depicts an exemplary MRI system in accordance with various embodiments.

In various embodiments, the imager 112 is an MRI apparatus. With reference to FIG. 2, the MRI apparatus 200 may include a cylindrical electromagnet 204, which generates the requisite static magnetic field within a bore 206 of the electromagnet 204. During medical procedures, a patient is placed inside the bore 206 on a movable support cradle 208. A region of interest 210 within the patient (e.g., the patient's head) may be positioned within an imaging region 212 wherein the electromagnet 204 generates a substantially homogeneous field. A set of cylindrical magnet field gradient coils 213 may also be provided within the bore 206 and surrounding the patient. The gradient coils 213 generate magnetic field gradients of predetermined magnitudes, at predetermined times, and in three mutually orthogonal directions. With the field gradients, different spatial locations can be associated with different precession frequencies, thereby giving an MR image its spatial resolution. An RF transmitter coil 214 surrounding the imaging region 212 emits RF pulses into the imaging region 212, and receives MR response signals emitted from the region of interest 210. (Alternatively, separate MR transmitter and receiver coils may be used.)

The MRI apparatus 200 generally includes an MRI controller 216 that controls the pulse sequence, i.e., the relative timing and strengths of the magnetic field gradients and the RF excitation pulses and response detection periods. The MRI controller 216 may be combined with the transducer controller 108 into an integrated system control facility.

The MR response signals are amplified, conditioned, and digitized into raw data using an image processing system, and further transformed into arrays of image data by methods known to those of ordinary skill in the art. The image processing system may be part of the MRI controller 216, or may be a separate device (e.g., a general-purpose computer containing image processing software) in communication with the MRI controller 216 and/or the transducer controller 108. Because the response signal is tissue- and temperature-dependent, it facilitates identifying the treatment target region 117 in the image, as well as computing a temperature map from the image. Further, the acoustic field resulting from ultrasound application may be monitored in real-time, using, e.g., thermal MRI or MR-based acoustic radiation force imaging. Thus, using MRI data, the ultrasound transducer 102 may be driven so as to focus ultrasound into (or near) the treatment region 117 while the temperature of the target and surrounding tissues and/or the acoustic field intensity are being monitored.

Figure 3A:
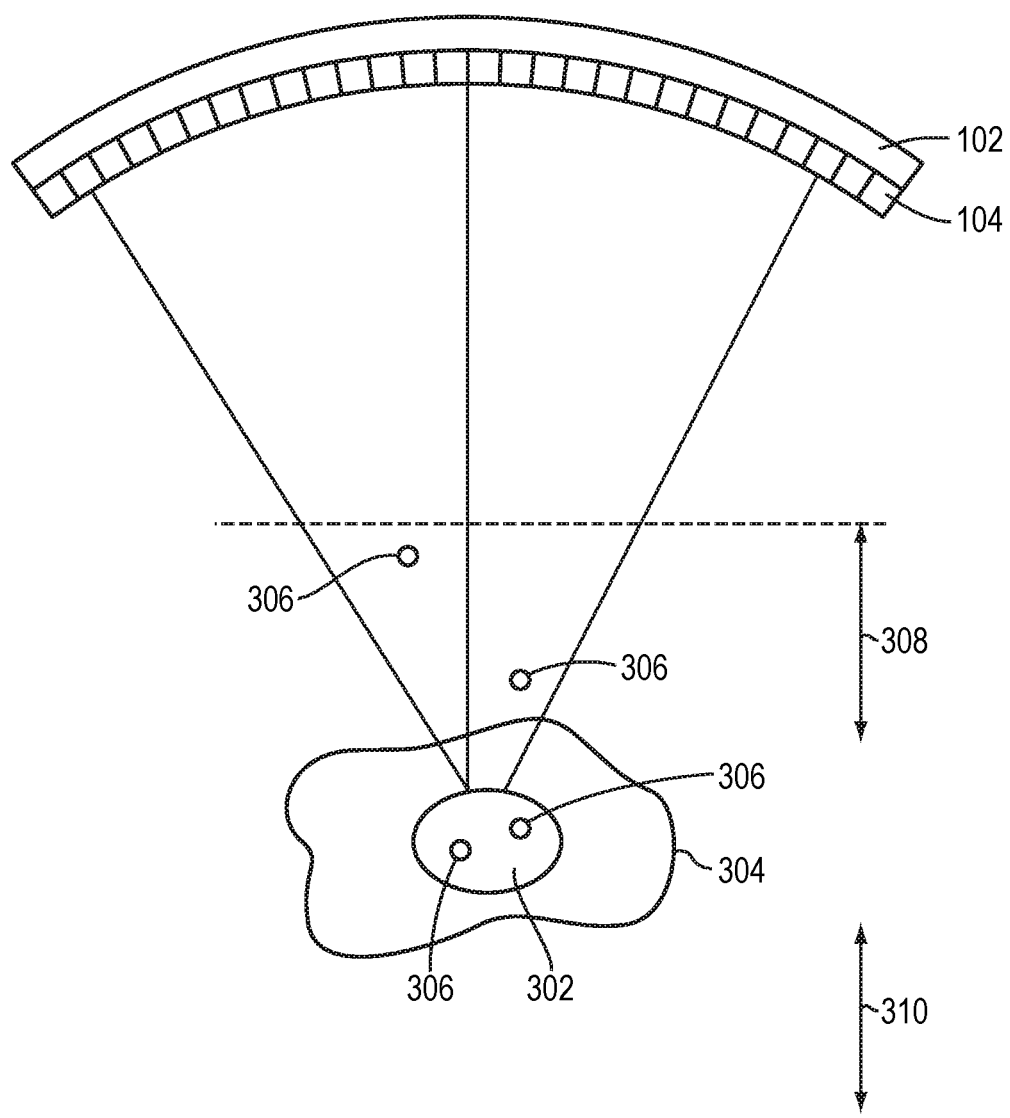
FIG. 3A schematically illustrates hot spots generated in the focal and/or non-focal zones in accordance with various embodiments.

Referring to FIG. 3A, during a focused ultrasound procedure, the transducer elements 104 are activated to transmit waves that collectively converge into a focus at a focal zone 302 corresponding to (or within) the target tissue region 304. The energy density (intensity) in the focal zone 302 may or may not be uniform. For example, one or more "hot spots" 306 may occur; the hot spots 306 in the focal zone 302 can cause excessive heat and significant pain to the patient. In addition, due to tissue inhomogeneity, there may be hot spots 306 at locations other than the focal zone 302. For example, the hot spots 306 may occur in the "near field," i.e., a region 308 between the transducer array 102 and the focal zone 302, as well as in the "far field," i.e., a region 310 beyond the focal zone 302. Such hot spots may lead to undesired necrosis of non-targeted tissue in the near and/or far field.

To minimize the undesired hot spots 306 in the focal and/or non-focal zones, in various embodiments, the imager 112 (such as the MRI apparatus 200) monitors a temperature distribution and/or an acoustic field intensity distribution in the target and surrounding tissues; based on the monitored information, locations of the hot spots can be identified. In one implementation, based on the identified hot spot locations, transducer parameters (such as frequencies, amplitudes, and/or phases of the transducer elements 104 and a sonication time) may be adjusted as further described below to minimize the hot spots 306, thereby achieving a substantially uniform temperature distribution in the focal zone and/or non-focal zone. As used herein, a "substantially uniform" or "uniform" temperature distribution in a predefined volume means that the maximum temperature difference between points within the predefined uniform volume is less than 20% of the average temperature in the set volume, preferably less than 10%, more preferably less than 5%.

Figure 3B:
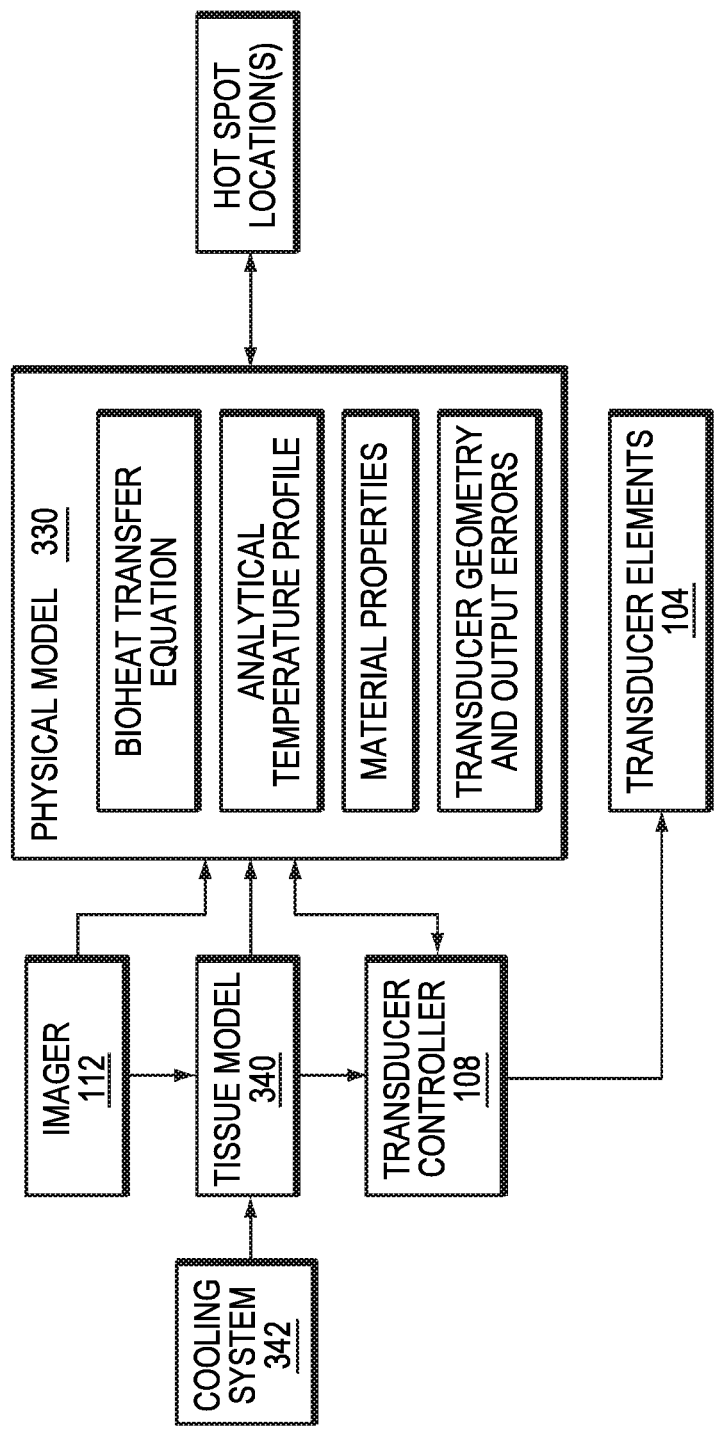
FIG. 3B schematically illustrates a physical model for predicting locations of hot spots in accordance with various embodiments.

Referring to FIG. 3B, in various embodiments, a predictive physical model 330 is used to predict the locations of the hot spots prior to activation of the transducers. The prediction model may be implemented in the controller 108 or in another computational entity (including a suitable processor and memory) within, or in communication with, the system 100, and may utilize information acquired using the imager 112. For example, the MRI apparatus 200 may monitor the temperature and/or an acoustic field intensity distribution in the near field during a first few sonications of the focused ultrasound procedure prior to formation of the hot spots. Based on this information, the physical model 330 may predict the expected locations of hot spots in the near field as well as extend the prediction into the focal region and/or far field. In one embodiment, the physical model 330 utilizes at least one differential (or integral) equation that describes the temperature evolution and/or heating process in tissue, taking into account, for example, heat transfer through thermal conduction or blood perfusion, metabolic heat generation, and/or absorption of energy applied to the tissue—e.g., the well-known Pennes bioheat transfer equation. The differential equation, supplemented by suitable initial and/or boundary conditions (e.g., a known temperature profile at the beginning of treatment, or a fixed temperature at a boundary of the zone of interest), may be straightfowardly solved numerically (or, in certain cases, analytically) to simulate temperature evolution and heating processes in the zone of interest, and thereby predict the temperature as a function of time and/or space (or at one or more selected discrete points in time and space). Uncertainties in parameters of the model, such as tissue and blood-flow parameters and speed of sound in the different tissues, can generally result in prediction inaccuracies. In some embodiments, these uncertainties are reduced by adjusting the model parameters based on a comparison of the temperature prediction with a temperature distribution measured in a successive sonication, e.g., using estimation theory or regression to minimize the differences.

The physical model 330 need not necessarily simulate biophysically the temperature evolution and/or heating process in tissue. Rather, in some embodiments, the physical model 330 utilizes an analytical temperature profile (e.g., a combination of polynomial or other functions) with adjustable coefficients. Upon acquisition of the measured temperature and/or an acoustic field intensity distribution in the near field from the imager 112, the model coefficients are adjusted to fit the profile to the measurements, i.e., to minimize the error between the measured and predicted temperatures.

It should be stressed that acquiring information about the temperature and/or acoustic field intensity distribution during the focused ultrasound procedure may not be necessary to predict the locations of the hot spots. In various embodiments, the physical model 330 predicts the temperature distribution in the focal and non-focal zones based on stored information about the geometry of the transducer elements 104 and their locations and orientations relative to the target region 304 as well as the amplitudes, frequencies and phases of ultrasound waves that will be transmitted from the elements 104. In addition, the physical model 330 may take into account transducer output errors (indicated at 335) resulting from, for example, a deviation of electrical impedance from the assumed/measured value or transducer elements 104 moving or shifting from their expected location during manufacturing, use and repair and/or as a result of the elements 104 being deformed by heat. Approaches to determining transducer output errors are provided, for example, in U.S. Pat. No. 7,535,794, the contents of which are incorporated herein by reference.

Further, the physical model 330 may utilize parameters, such as material properties (e.g., the energy absorption of the tissue at the employed frequency or the speed of sound) along the beam path. The material properties may be collected using the imager 112 as described above and/or other suitable devices. For example, if the tissue surrounding the target and traversed by the ultrasound is a patient's skull, CT imaging may be used to extract the anatomical characteristics (such as the skull thickness, skull layers, local bone densities and/or directional or geometrical features including a normal relative to a surface region or an approximated curvature) of the skull. Methods of creating a local geometric model or mapping of the skull regions 216 are described, for example, in U.S. Patent Publication No. 2010/0179425, the entire disclosure of which is hereby incorporated by reference. In addition, the structural inhomogeneity of the skull may be characterized using an indicator that can be quantified at the microstructure level of the skull; the indicator is determined based on the skull density measured in images acquired using an imager 112. A suitable method is described in U.S. Patent Publication No. 2016/0184026, the entire disclosure of which is hereby incorporated by reference.

The physical model 330 may analyze acoustic paths through various skull regions, performing thermal simulations to estimate how different skull regions reflect and/or absorb different quantities of energy and have different heating profiles, and predict the location of the focal zone, the temperature distribution in the focal and non-focal zones, and the locations of the hot spots 306.

After the expected locations of the hot spots 306 are identified (by measurements and/or prediction by the physical model 330), various approaches may be utilized to compensate for or minimize the hot spots. For example, a tissue model 340 characterizing the material characteristics of the target and/or surrounding tissue may be used to identify one or more regions near the expected hot spot locations that have less heat sensitivity and/or can tolerate higher thermal energy relative to other tissues near the expected locations of the hot spots. The tissue model 340 may take the form of a three-dimensional table of cells corresponding to voxels representing the target and surrounding tissue; the values of the cells represent characteristics of the tissue, such as heat tolerance, that are relevant to management of hot spots. The voxels are obtained tomographically by the imager 112 and the type of tissue that each voxel represents can be determined automatically by conventional tissue-analysis software. Using the determined tissue types and a lookup table of tissue parameters (e.g., heat tolerance by type of tissue), the cells of the tissue model 340 are populated. Further detail regarding creation of a tissue model that identifies the heat sensitivity and/or thermal energy tolerance of various tissues may be found in U.S. Patent Publication No. 2012/0029396, the entire disclosure of which is hereby incorporated by reference.

In various embodiments, a higher tissue tolerance to heat is achieved by actively cooling the tissue using a cooling system (e.g., a heat exchanger) 342 integral with the transducer array 102. The integrated cooling system 342 may include an accessible tissue interface (typically, the skin or a cavity that is accessible from outside the body) in contact with a heat exchanger (or source), preferably located in the vicinity of the tissue to be cooled (or heated). The heat exchanger may, for example, take the form of a balloon that conforms to the surface it is to cool, or of a fixed shape immersed in water that is in contact with the body surface. The rate of cooling may be controlled, for example, via the flow rate of coolant through the heat exchanger, or via the temperature of the coolant. The cooling system may also be provided by solid heat-conducting components such as bi-metal plates or stripes placed in contact with the skin and whose temperature may be controlled electronically. The cooling element 342 may be manually or automatically controlled.

Figure 4A:
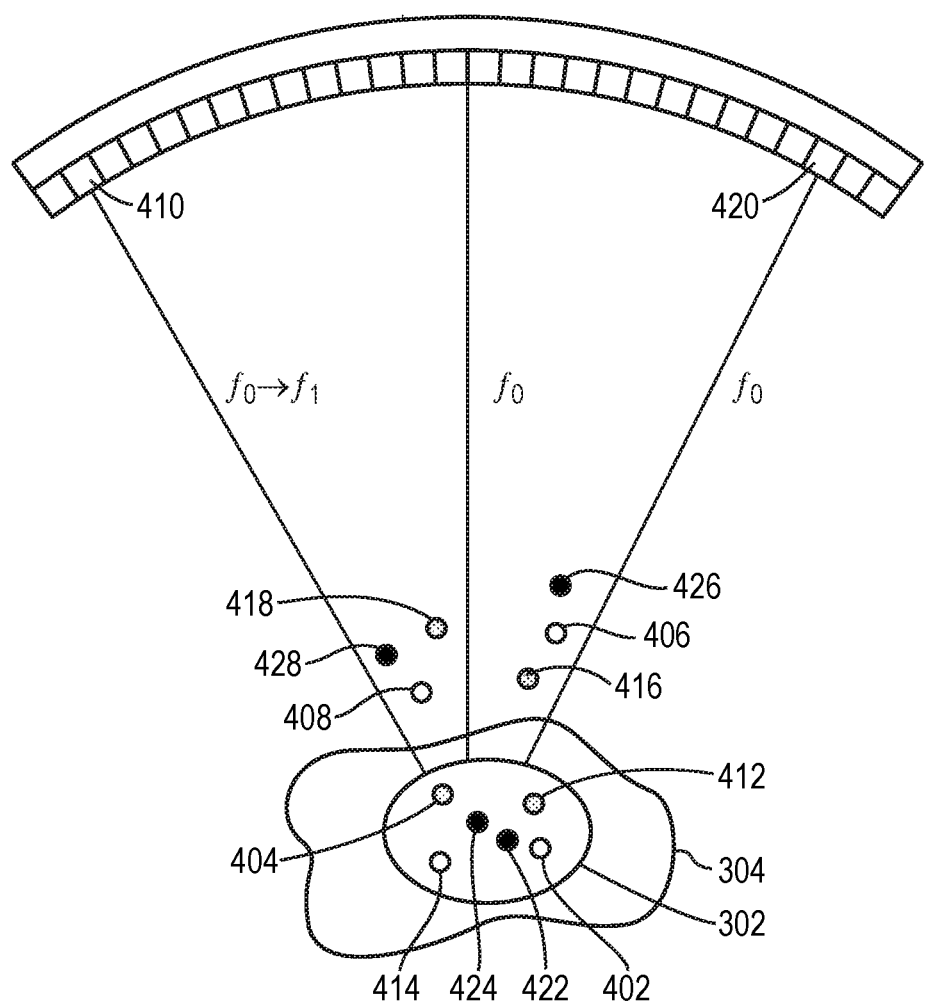
FIGS. 4A-4E depict various approaches of adjusting operations of an ultrasound system for compensating for the hot spots in accordance with various embodiments.

Once the tissue regions tolerant to relatively high temperatures are identified in the tissue model 340, the physical model may inversely compute the required frequency associated with at least one transducer element so that hot spots will occur within these tissues. This inverse computation is possible because an interference pattern of a first ultrasound wave with other ultrasound waves can be varied by varying the frequency of the first ultrasound wave; and changing the interference pattern alters the locations where hot spots occur. For example, referring to FIG. 4A, when the ultrasound waves emitted from the transducer elements 104 have the same frequency $f_o$, the locations of the hot spots may be expected to occur at locations 402-408 based on measurements and/or a model prediction as described above. By adjusting the frequency of a transducer element 410 from $f_o$ to $f_1$, the hot spots may be expected to occur at different positions 412-418; similarly changing the frequency of the transducer element 420 may cause the hot spots to move to other locations 422-428. Movement of the hot spot locations may reduce the absorbed energy at a specific point (hot spot). Accordingly, in various embodiments, the physical model 330 inversely computes the dynamically varying frequencies associated with the transducer elements 410, 420 based on the identified redistributed locations 412-418, 422-428 that may have lower heat sensitivity and/or can tolerate high thermal energy to thereby cause movement of the hot spots so as to reduce the accumulated energy (hence the temperature rise) at specific hot spots. Therefore, this approach minimizes tissue damage at the target region and/or non-target region by averaging the energy over several hot spots or directing hot spots to region(s) having low-heat sensitivity and/or high-thermal-energy tolerance.

As noted, the transducer controller 108 may implement the physical model 330 and/or the tissue model 340, or may instead be responsive to the physical model and address the tissue model as needed. In any case, the transducer controller 108 may not only compute the ultrasound frequency (or frequencies) that create hot spots at the locations 412-418, 422-428, but may also dynamically varies this frequency (or frequencies) with time. In this way, the transducer controller 108 causes the locations of the hot spots to shift back and forth between the expected locations. This represents another control factor that accommodates the characteristics of the tissue in and around the target tissue, ensuring that the hot spots do not persist at any one location for an amount of time that will cause a clinically adverse effect to any of the tissues. Accordingly, the accumulated energy (and the resulting temperature rise) at a specific hot spot is reduced since within a predefined time interval the hot spot may jump between different locations.

Alternatively, the transducer controller 108 may randomly vary the frequency of the transducer element(s). This may cause the hot spots to occur at various locations—i.e., from locations 402-408 to locations 412-418, and then to locations 422-428. Tissues in the redistributed hot spot locations 412-418, 422-428 in this embodiment do not necessarily have less heat sensitivity and/or tolerate higher thermal energy than tissues at the expected hot spot locations 402-408, but they are preferably different from one another and different from the measured/predicted hot spot locations 402-408. Temporal adjustments of the ultrasound frequencies may disperse ultrasound energy from a relatively smaller number of hot spot locations 402-408 to a larger number of hot spot locations 402-408, 412-418, and 422-428. This approach may reduce the energy accumulation at a specific hot spot by dispersing the energy between multiple spots. The frequencies associated with transducer elements may be varied discretely or continuously. In addition, they may be varied periodically during sonications of the focused ultrasound procedure.

The location of the focal zone 302 may change due to varying the frequencies of the transmitted waves. In some embodiments, the phases and/or amplitudes of the drive signals provided to the transducer elements 104 are simultaneously adjusted with the frequencies in order to maintain the focus at the target tissue region 304. Again, adjustments of the phases and/or amplitudes may be determined using the physical model.

Figure 4B:
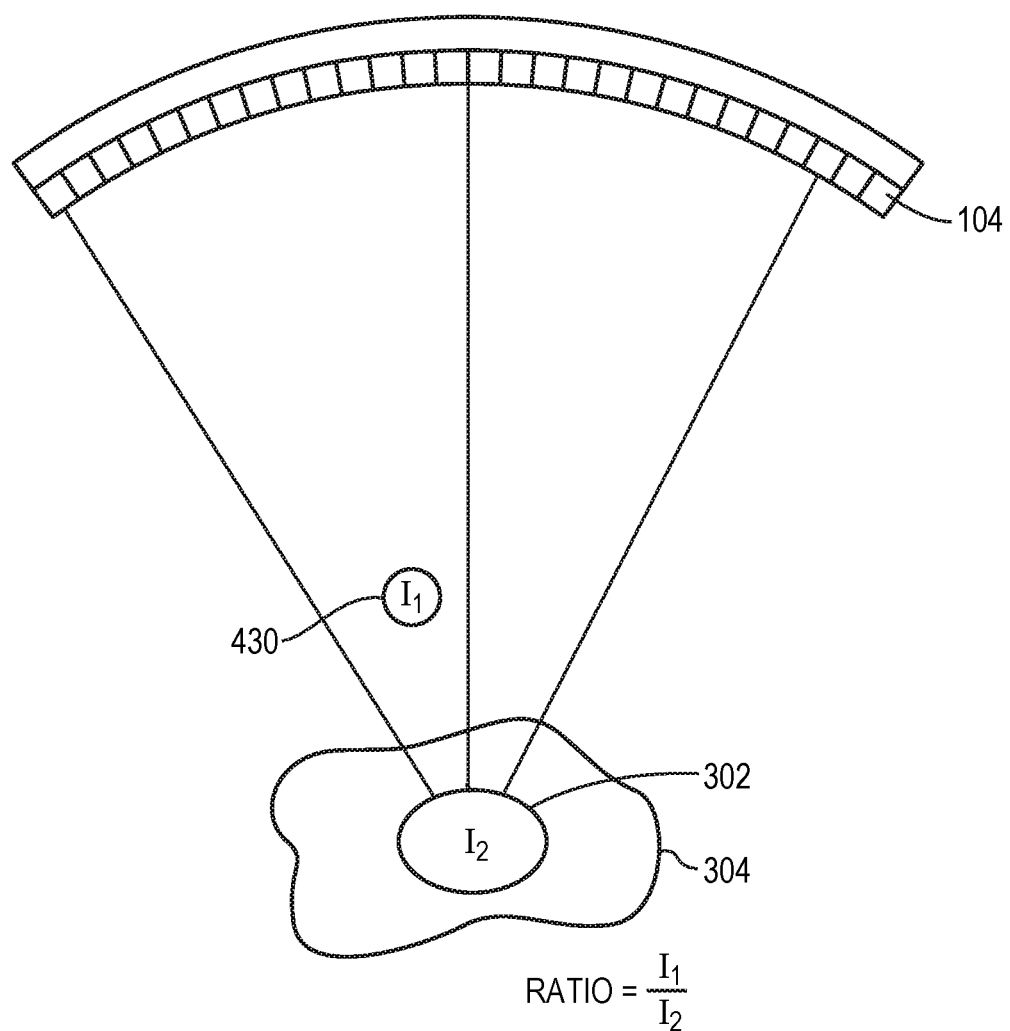

Additionally or alternatively, the physical model 330 may adjust (or result in adjustment of) other parameter values associated with the transducer elements 104 to account for the hot spots. For example, referring to FIG. 4B, the physical model 330 may simulate the effects on the ratio of the maximal intensity, $I_1$, in a hot spot 430 to the maximal intensity, $I_2$, in the focal zone 302 based on simulated variations in the output intensities of at least some transducer elements 104. Based on the simulated effects, the wave intensities and/or wave phases of some transducer elements 104 may be adjusted in order to decrease the computed intensity ratio, thereby reducing the effects of temperature non-uniformity caused by the hot spots. For example, the physical model 330 may explore the space of possible variations in transducer intensities constrained by the need to maintain a minimum intensity at the focus. Using the Simplex algorithm or other conventional linear-programming technique, this constraint makes the simulation computationally tractable and guarantees that either a solution will be found or is not possible.

Figure 4C:
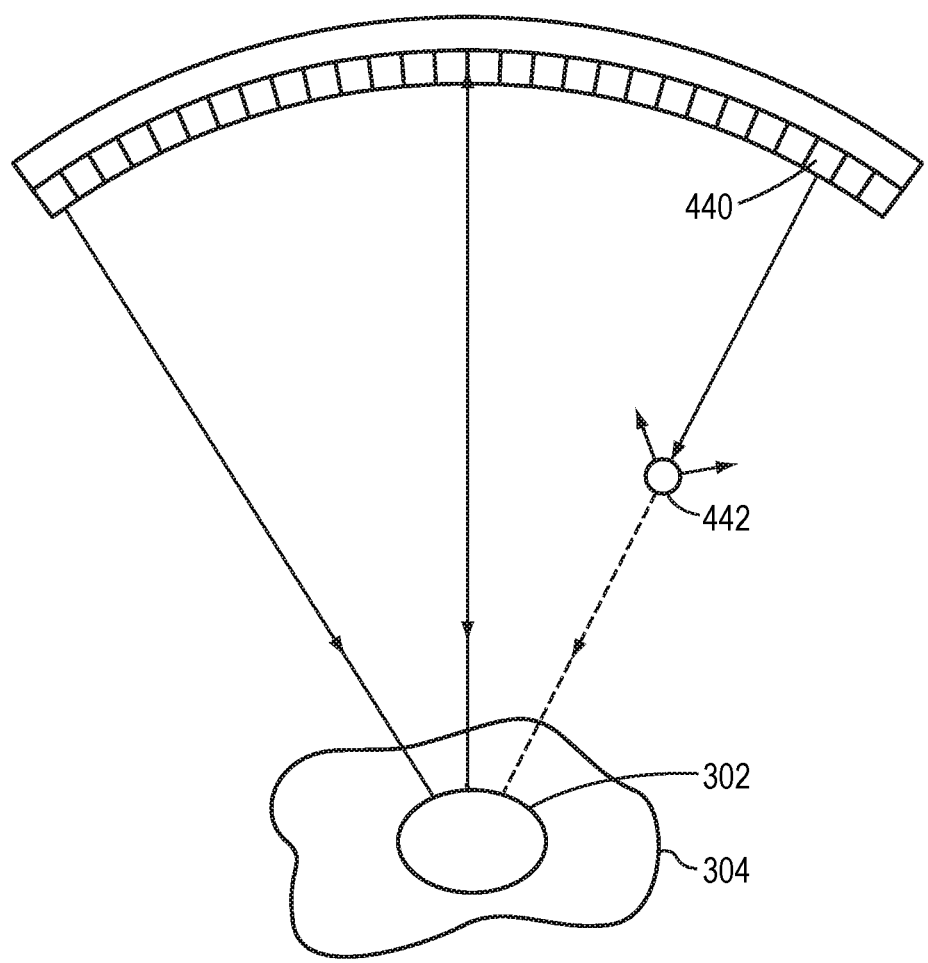

In still other embodiments, with reference to FIG. 4C, the physical model 330 estimates an acoustic energy at the focal zone 302 contributed from each transducer element 104 after traversing the surrounding tissue. Additionally or alternatively, the energy contribution from the element 104 may be measured using, for example, acoustic radiation force impulse (ARFI) imaging. If the contribution from a transducer element 440 at the focal zone is below a threshold, it will be due to excessive reflection and/or absorption of energy emitted from the element 440 by the traversed tissue surrounding the target 304; this reflection and/or absorption energy may likely result in a hot spot 442. Accordingly, in one implementation, the intensities of the waves transmitted from the transducer elements 104 whose energy contribution at the focal zone 302 is below the threshold may be decreased to reduce the likelihood of generating intervening hot spots.

Figure 4D:
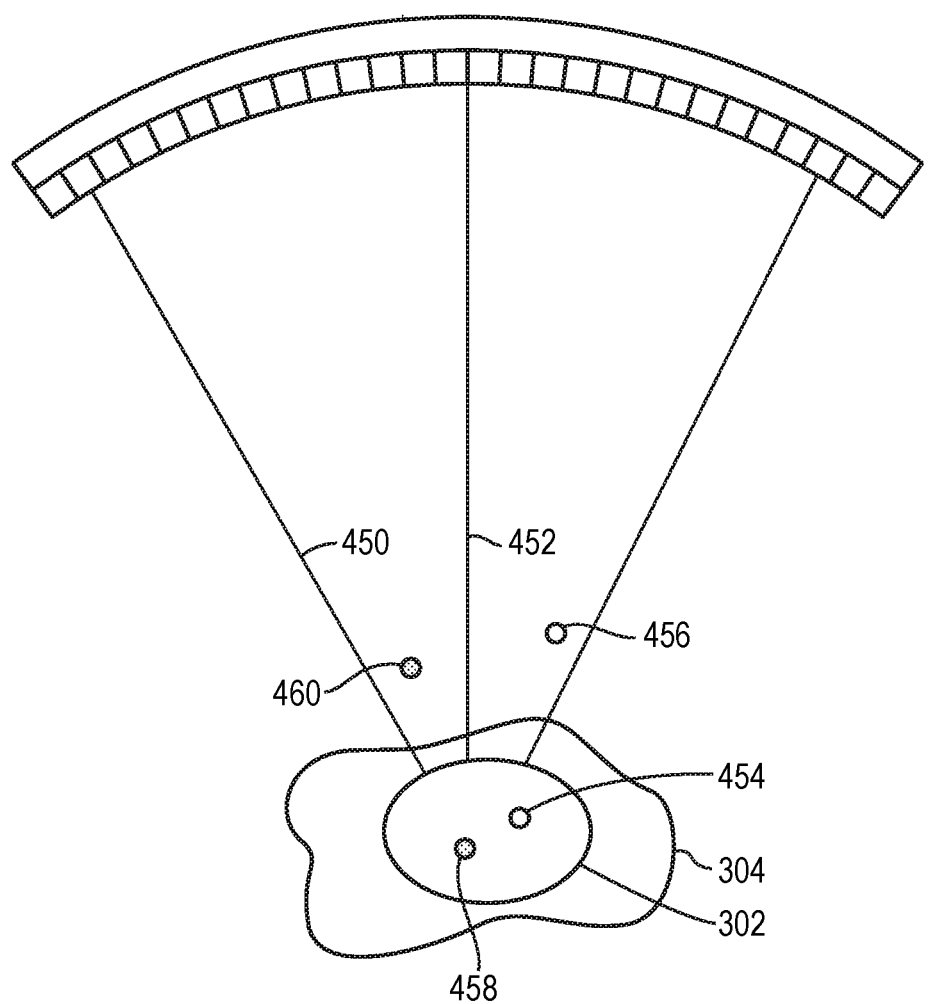

In various embodiments, beamforming is used to reduce or eliminate the hot spots, or to shift them dynamically so that the average energy remains below a clinically acceptable maximum (relative to the heat tolerance of tissues in the beam path, as described above); in particular, the beamforming is used to control the interference pattern of the transmitted ultrasound waves. For example, time delays associated with some transducer elements may be adjusted to generate time-varying interference patterns. Again, because each interference pattern may have wave amplifications (e.g., sufficiently large to qualify as hot spots) at different locations, dynamically varying the time delays associated with at least some transducer elements may redistribute the energy of undesired hot spots to various locations. For example, with reference to FIG. 4D, when the ultrasound waves 450, 452 emitted from two transducer elements have a time delay $d_1$ between them, the locations of the hot spots may occur at locations 454, 456. By adjusting the time delay from $d_1$ to $d_2$, the locations of the hot spots occur at different positions 458, 460. Distributing the hot spots to various locations may thus even out the resulting temperature distribution.

Figure 4E:
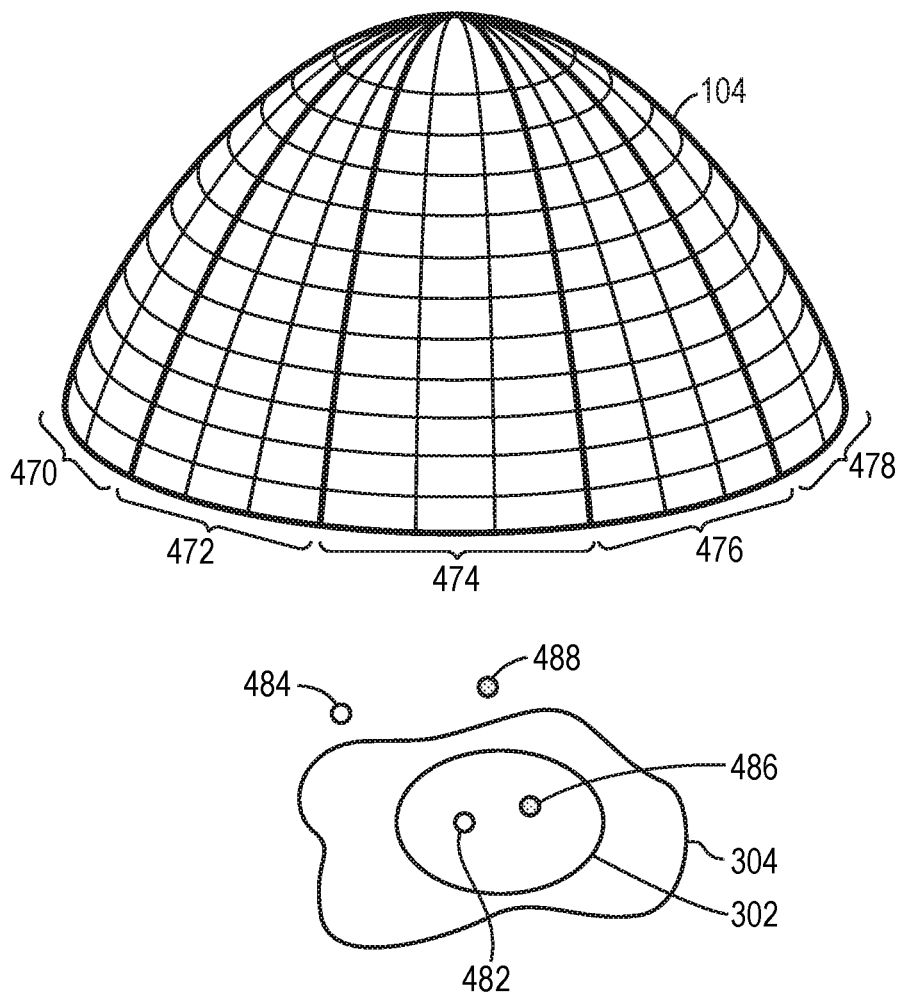

Compensation for hot spots may also be achieved by selectively activating and deactivating at least some transducer elements. Referring to FIG. 4E, in various embodiments, the transducer array 102 is divided into multiple sub-regions 470-478; each sub-region comprises a one- or two-dimensional array (i.e., a row or a matrix) of transducer elements 104. The sub-regions 470-478 may be separately controllable, i.e., they are each capable of emitting ultrasound waves at amplitudes, frequencies, and/or phases that are independent of the amplitudes, frequencies and/or phases of the other sub-regions 470-478. In one embodiment, the sub-regions 470-478 are selectively activated and deactivated, one at a time, to transmit ultrasound to the target region; each sub-region may be assigned different amplitudes, frequencies, and/or phases from one another as determined by the physical model. As depicted in FIG. 4E, activation of the sub-region 470 may generate the focal zone 302 at the target region 304 and undesired hot spots at locations 482, 484; whereas activation of another sub-region 474 may generate a focused beam at the same focal zone 302 but with undesired hot spots at locations 486, 488 different from the locations 482, 484. Accordingly, activation of different sub-regions may generate a common focal zone 302 at the target region 304 but with undesired hot spots at different locations 482-488 in the surrounding tissue. Thus, by selectively activating and deactivating different sub-regions 470-478 of the transducer elements 104, the hot spots may be distributed among various locations so they do not persist at any one location for an amount of time that will cause a clinically adverse effect on non-target tissue. This energy dispersion improves the uniformity of the resulting temperature distribution and prevents tissue damage due to hot spots.

Figure 5:
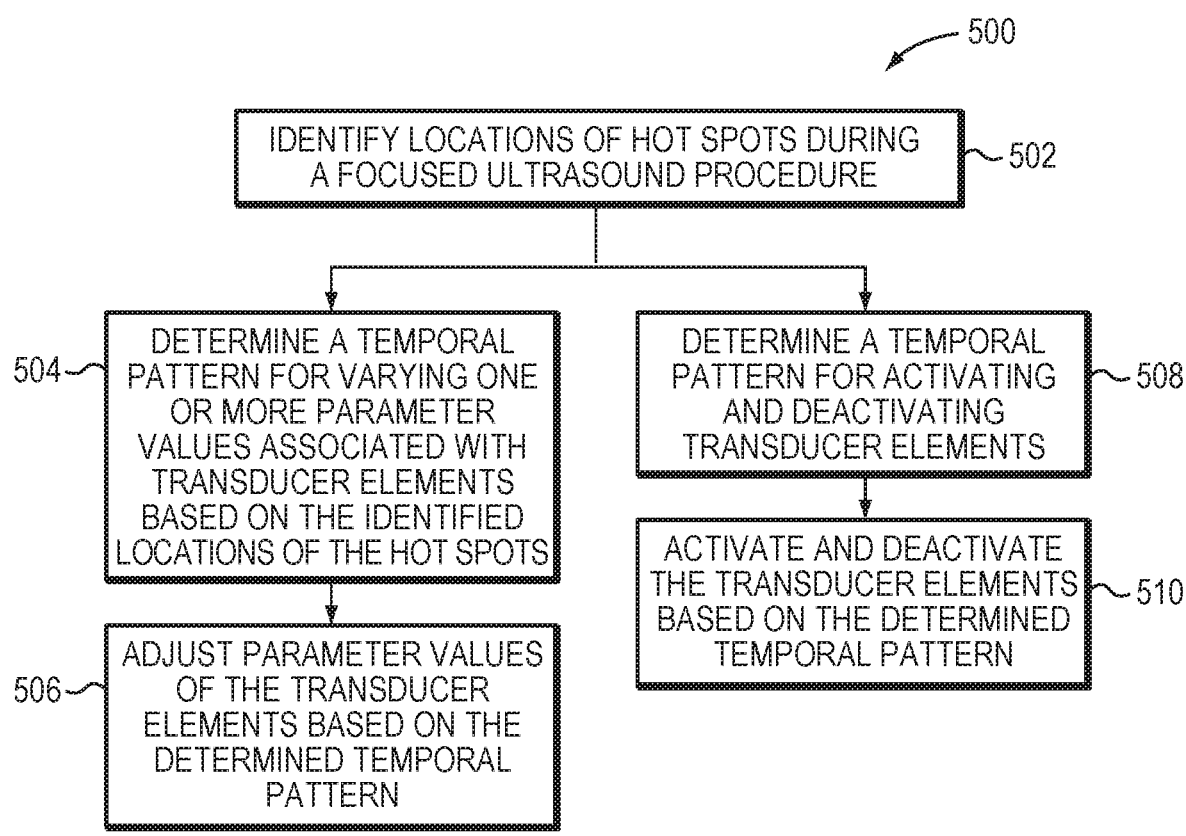
FIG. 5 is a flow chart illustrating an approach for minimizing hot spots in the target and surrounding tissues during a focused ultrasound procedure in accordance with various embodiments.

FIG. 5 is a flow chart 500 illustrating an approach for minimizing hot spots in the target and surrounding tissues during a focused ultrasound procedure in accordance with various embodiments. In a first step 502, the locations of the hot spots are identified during the ultrasound procedure. For example, the hot spot locations may be identified and localized using an imager. Alternatively, the imager may measure the temperature and/or acoustic field intensity distribution in the near field during the first few sonications; based on the measured temperature and/or acoustic field intensity distribution, a physical model may predict the locations of the hot spots in the near field, focal zone, and/or far field. In some embodiments, the imager is used to identify the location of the target (and/or the transducer elements); no measurements on the temperature and/or acoustic field intensity distribution are required. The physical model can predict the hot spot locations based on the geometry of the transducer elements and their locations and orientations relative to the target region, the amplitudes, frequencies, and phases of ultrasound waves, and/or the material properties of the target and surrounding tissues. In a second step 504, based on the measured and/or predicted locations of the hot spots, the physical model may determine a temporal pattern for varying one or more parameter values (e.g., frequencies, amplitudes, and/or time delays) associated with the transducer elements in order to compensate for the hot spots. In a third step, parameter values of the transducer elements are adjusted based on the determined temporal pattern (step 506). In some embodiments, the physical model determines a temporal pattern for activating and deactivating each sub-region of the transducer elements for compensating for the hot spots based on the identified hot spot locations (step 508). The transducer elements are then activated and deactivated based on the determined temporal pattern (step 510). Accordingly, the current invention provides various approaches that effectively minimize hot spots generated in the focal and non-focal zones; this advantageously allow the target region to be uniformly heated while avoiding the surrounding healthy tissue to be damaged.

In general, functionality for minimizing the hot spots in the target and/or surrounding tissues, including, analyzing imaging data of the target and surrounding tissues acquired using an imager, determining a temperature and/or acoustic field intensity distribution in the target and/or surrounding tissue based on the imaging data, identifying the hot spots located in the target and/or surrounding tissue, acquiring material characteristics of the target and/or surrounding tissue (using a predictive physical model, the imager, and/or measurements of ultrasound transmission and/or reflections from the skull), predicting the locations of the hot spots in the target and surrounding tissues, computing a temporally varying pattern or adjustments of the transducer parameter values (e.g., frequencies, amplitudes, time delays, etc.) and/or activation and deactivation of sub-regions of the transducer array, as described above, whether integrated within a controller of the imager, and/or an ultrasound system, or provided by a separate external controller or other computational entity or entities, may be structured in one or more modules implemented in hardware, software, or a combination of both. For embodiments in which the functions are provided as one or more software programs, the programs may be written in any of a number of high level languages such as FORTRAN, PASCAL, JAVA, C, C++, C#, BASIC, various scripting languages, and/or HTML. Additionally, the software can be implemented in an assembly language directed to the microprocessor resident on a target computer (e.g., the controller); for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

In addition, the term "controller" used herein broadly includes all necessary hardware components and/or software modules utilized to perform any functionality as described above; the controller may include multiple hardware components and/or software modules and the functionality can be spread among different components and/or modules.

Certain embodiments of the present invention are described above. It is, however, expressly noted that the present invention is not limited to those embodiments; rather, additions and modifications to what is expressly described herein are also included within the scope of the invention.

What is claimed is:

1. A method of heating a target region using an ultrasound transducer comprising a plurality of transducer elements for generating a focal zone at the target region, the method comprising:
   (a) dividing the ultrasound transducer into a plurality of sub-regions, each sub-region comprising a plurality of transducer elements;
   (b) operating the sub-regions in accordance with an activation and deactivation pattern in which at least one of the sub-regions is activated;
   (c) identifying a first location of at least one hot spot, different from the focal zone, in at least one of the target region or a region surrounding the target region during an ultrasound sonication process, the hot spot having an energy density above a predefined acceptable level;
   (d) selecting a second location of the at least one hot spot, the second location being different from the first location and, compared to the first location, being low-heat sensitive and/or high-thermal-energy tolerant;
   (e) based at least in part on the identified first and second locations of the at least one hot spot, altering the activation and deactivation pattern of the sub-regions such that the at least one hot spot is generated at the second location to thereby reduce the energy density of the first location to the predefined acceptable level while maintaining the focal zone at the target region, wherein following the alteration of the activation and deactivation pattern, at least one of the sub-regions is activated; and
   (f) operating the sub-regions of the transducer elements in accordance with the altered activation and deactivation pattern.

2. The method of claim 1, wherein the activation and deactivation pattern creates a substantially uniform temperature distribution in the target region.

3. The method of claim 1, further comprising acquiring imaging data of the target region and the surrounding region and, based thereon, determining a temperature distribution in the target region and the surrounding region, at least one of the first or second location of the at least one hot spot being identified based on the temperature distribution.

4. The method of claim 1, further comprising acquiring imaging data of at least one of the target region or the surrounding region and, based thereon, determining an acoustic field distribution therein, at least one of the first or second location of the at least one hot spot being identified based on the acoustic field distribution.

5. The method of claim 1, further comprising acquiring imaging data of the surrounding region and, based thereon, generating a predicted temperature distribution in the target region and the surrounding region using a prediction model, at least one of the first or second location of the at least one hot spot being identified based on the predicted temperature distribution.

6. The method of claim 5, wherein the imaging data is ARFI data.

7. The method of claim 1, wherein at least one of the first or second location of the at least one hot spot is identified based at least in part on a prediction model.

8. The method of claim 1, further comprising the step of identifying additional hot spots, the activation and deactivation pattern distributing the hot spots among different locations so the hot spots do not persist at any single location for an amount of time that will cause a clinically adverse effect on non-target tissue.

9. A system for heating a target region, the system comprising an ultrasound transducer comprising a plurality of transducer elements for generating a focal zone at the target region, and
   a controller configured to:
   (a) divide the ultrasound transducer into a plurality of sub-regions, each sub-region comprising a plurality of transducer elements;
   (b) operate the sub-regions in accordance with an activation and deactivation pattern in which at least one of the sub-regions is activated;
   (c) identify a first location of at least one hot spot, different from the focal zone, in at least one of the target region or a region surrounding the target region during an ultrasound sonication process, the hot spot having an energy density above a predefined acceptable level;
   (d) select a second location of the at least one hot spot, the second location being different from the first location and, compared to the first location, being low-heat sensitive and/or high-thermal-energy tolerant;
   (e) based at least in part on the identified first and second locations of the at least one hot spot, altering the activation and deactivation pattern of the sub-regions such that the at least one hot spot is generated at the second location to thereby reduce the energy density of the first location to the predefined acceptable level while maintaining the focal zone at the target region, wherein following the alteration of the activation and deactivation pattern, at least one of the sub-regions is activated; and
   (f) operate the sub-regions of the transducer elements in accordance with the altered activation and deactivation pattern.

10. The system of claim 9, wherein the activation and deactivation pattern creates a substantially uniform temperature distribution in the target region.

11. The system of claim 9, further comprising an imager, coupled to the controller, for acquiring imaging data of the target region and the surrounding region, wherein the controller is further configured to determine a temperature distribution in the target region and the surrounding region based on the imaging data and identify at least one of the first or second location of the at least one hot spot based on the temperature distribution.

12. The system of claim 9, further comprising an imager, coupled to the controller, for acquiring imaging data of at least one of the target region or the surrounding region, wherein the controller is further configured to determine an acoustic field distribution therein based on the imaging data, at least one of the first or second location of the at least one hot spot being identified based on the acoustic field distribution.

13. The system of claim 12, wherein the imager is an ARFI device.

14. The system of claim 9, further comprising an imager, coupled to the controller, for acquiring imaging data of the surrounding region, wherein the controller is further configured to generate a predicted temperature distribution in the target region and the surrounding region based on the imaging data and a physical model and identify at least one of the first or second location of the at least one hot spot based on the predicted temperature distribution.

15. The system of claim 9, wherein the controller is further configured to identify at least one of the first or second location of the at least one hot spot based at least in part on a prediction model.

\* \* \* \* \*